(12) United States Patent
Wang (10) Patent No.: US 6,629,039 B1
(45) Date of Patent: Sep. 30, 2003

(54) METHOD AND APPARATUS FOR IMPURITY DETECTION

(75) Inventor: Yongdong Wang, Wilton, CT (US)

(73) Assignee: PerkinElmer Instruments LLC, Shelton, CT (US)

( * ) Notice: Subject to any disclaimer, the term of this patent is extended or adjusted under 35 U.S.C. 154(b) by 0 days.

(21) Appl. No.: 09/561,600

(22) Filed: Apr. 27, 2000

(51) Int. Cl.⁷ .......................... G01N 31/00; G06F 19/00
(52) U.S. Cl. ........................ 702/22; 702/23; 702/24; 702/25
(58) Field of Search .................. 702/22; 422/70, 422/56; 73/31.03

(56) References Cited

U.S. PATENT DOCUMENTS

| | | | | |
|---|---|---|---|---|
| 3,863,489 A | * | 2/1975 | Ayers et al. ............... 73/31.03 |
| 4,353,242 A | * | 10/1982 | Harris et al. .................. 422/56 |
| 4,482,966 A | * | 11/1984 | Mito et al. ..................... 702/32 |
| 4,544,840 A | * | 10/1985 | Keller ........................... 422/70 |
| 4,740,903 A | * | 4/1988 | Nakatsuka et al. ........... 702/32 |
| 4,807,148 A | * | 2/1989 | Lacey ........................... 702/32 |
| 4,824,639 A | * | 4/1989 | Hildenbrand et al. ......... 422/56 |
| 4,835,708 A | * | 5/1989 | Frans ........................... 702/27 |
| 5,138,869 A | * | 8/1992 | Tom .......................... 73/31.03 |
| 5,596,135 A | * | 1/1997 | Mito et al. ................. 73/23.35 |
| 5,783,450 A | * | 7/1998 | Yoshida et al. ............... 422/70 |

\* cited by examiner

Primary Examiner—John Barlow
Assistant Examiner—Aditya Bhat
(74) Attorney, Agent, or Firm—St. Onge Steward Johnston & Reens LLC (57) ABSTRACT

A method and apparatus is provided for detecting an impurity in a sample where an index can be calculated to assess purity in the presence of n major components with signal averaging or noise-filtering automatically built-in. The method and apparatus can be applied to liquid chromatography impurity detection using UV-VIS spectrophotometry based on robust matrix algebra representing the entire spectral space generated by the sample.

12 Claims, 7 Drawing Sheets

METHOD AND APPARATUS FOR IMPURITY DETECTION

FIELD OF THE INVENTION

The invention relates to a method to detect an impurity in a sample which can be applied to chromatographic peak analysis through manipulation of spectrophotometric readings, and more particularly to readings detected from a photodiode-array (PDA) detector.

BACKGROUND OF THE INVENTION

Methods for the detection and identification of multiple components in a sample using the principles of liquid chromatography (LC) and spectrophotometry are well known to those skilled in the art. The identification of specific unknown components in the sample solution first requires a physical separation of any mixed components using liquid chromatography. The sample is eluted or washed through an LC column using a mobile phase of solvents known to be appropriate for the particular separation sought and system used. Separation is achieved with the LC column based upon a particular component's adsorptive affinity to the media packed in the LC column. The eluted sample is then analyzed using UV-VIS spectrophotometry. The particular chemical structure of the analyte when subjected to radiation in the ultraviolet-visible (UV-VIS) range of 200–800 nm will have a characteristic spectral response due to the absorption of radiation when detected with a photodiode-array (PDA) detector. The (PDA) detector measures the transmitted energy and converts it into absorption units (AU) as a function of elution time ($t_R$) and wavelength ($\lambda$).

Detection of impurities poses a problem when the particular chemical structure of the impurities is such that they become co-eluted with the analyte of interest. When this occurs the impurity is often difficult to detect because the chromatomographic separation does not sufficiently resolve the different components and their spectral peaks are overlapped. In the case of a single wavelength UV/visible detector one might see a "shoulder", "valley" or "excessive tailing" in the chromatographic peak to suspect the presence of an impurity. Moreover the absence of these features on the chromatographic peak does not assure that the component represented by the peak is pure. The impurity could simply be cloaked or "not seen" within the larger peak that is detected by the spectrophotometer because the chromatographic resolution was too low or the purity concentration was too low.

Several approaches have been taken to detect the presence of an impurity co-eluting with the analyte peak. M.V. Gorenstein, et al., "Detecting Co-Eluted Impurities by Spectral Comparison", LC-GC. 12, No. 10, 768–772 (1994), incorporated herein by reference, discloses a two-step spectral-contrast technique which first generates vector angles which measure the spectral heterogeneity of a given peak and the shape difference between two spectra. Then a quantification for non-ideal effects such as noise contribution is made and assigned as a threshold vector angle. These two angles are compared along an analyte's chromatogram. The procedure correlates the difference between the two angles with detection of an impurity in a chromatographic peak. However, in order to accomplish this there must be a baseline correction for each spectrum within the peak which involves interpolation of peak "start" and "end" spectra to obtain a series of underlying baseline spectra. In addition, the vector angles used to determine whether an impurity exists do not directly calculate or quantify the spectral error in the measured absorbence units caused by the impurity. Also, such a technique requires separate calibration runs to establish a threshold, and will have difficulties with multiple impurities.

Y. Hu, et al., "Assessment of Chromatographic Peak Purity By Means Of Artificial Neural Networks" J. Chromatogr. 734, 259–270 (1996), incorporated herein by reference, discloses a three-layer neural network for detecting the purity of a chromatographic peak. The method relies on applying a neural network to the difference between the spectra within the chromatographic peak to be analyzed. Applications of neural networks are known to those skilled in the art, and as disclosed by Hu in this application, involve training sets of data for the front half of each peak and testing these data sets for recognition responses against the back half of each peak using artificial neural network techniques. This approach strongly depends on the retention time and number of impurities with respect to the main components(s) due to the somewhat arbitrary partitioning between a front and back part of a chromatogram. Another disadvantage to this neural network approach is that approximately half of the data associated with a component's chromatogram and spectra are used which can compromise the detection sensitivity for analytes where the chromatographic retentions and spectra of the main component substance and impurity are strongly overlapped. Moreover, this approach is incapable of performing a quantitative analysis concerning impurity level.

What is desired, therefore, is a method to detect and quantify an impurity from an LC peak using UV-VIS spectrophotometry with a PDA detector where a measure of peak impurity can be reported in natural units across a whole chromatographic peak and where noise filtering is automatically built-in.

SUMMARY OF THE INVENTION

Accordingly, an object of the invention is to provide a method applying an algorithm for LC impurity detection where a peak purity index can be reported across the entire chromatographic peak.

Another object of the invention is to provide a method applying an algorithm for LC impurity detection that is not sensitive to detecting a peak start and a peak end for a chromatographic peak.

A further object of the invention is to provide a method applying an algorithm for LC impurity detection with signal averaging or noise-filtering automatically built-in.

Yet another object of the invention is to provide a method applying an algorithm for LC impurity detection which can detect not only an impurity co-existing with one major component but also an impurity in the presence of n major components.

Another object of the invention is to provide a method applying an algorithm for LC impurity detection where a peak index is reported in original spectral absorbence units which can be directly interpreted as the amount of spectral error caused by the impurity.

A further object of the invention is to provide a method applying an algorithm for LC impurity detection that requires no calibration or standard runs to detect the impurity.

Still another object of the invention is to provide a method applying an algorithm for LC impurity detection based on robust matrix algebra representing the entire spectral space corresponding to the chromatographic peak.

To overcome some of the disadvantages of the prior art and achieve some of the objects and advantages listed above, the present invention comprises: a method for detecting an impurity in a sample, and in a further aspect, an apparatus for detecting an impurity in a sample.

A method according to the invention for detecting an impurity in a sample having at least one analyte comprises the steps of: selecting a value representing an anticipated number of components in the sample; generating a matrix representing characteristic measurements for the sample, the characteristic measurements having at least two variables in each dimension; repeatedly selecting a subset within the matrix for analysis of the relation between the analyte and impurity; and calculating an index from the subset to assess purity of the sample.

The invention in one of its aspects also provides an apparatus for detecting an impurity in a sample having at least one component comprising: a device for obtaining characteristic measurements for the sample; a computer linked to the device; software executing on the computer for selecting a value representing an anticipated number of components in the sample; software executing on the computer for generating a matrix representing the characteristic measurements for the sample, the characteristic measurements having at least two variables in each dimension and; software executing on the computer for repeatedly selecting a subset within the matrix for analysis of the relation between the component and the impurity; and software executing on the computer for calculating an index from the subset to assess purity of the sample.

The invention and its particular features will become more apparent from the following detailed description with reference to the accompanying drawings.

DETAILED DESCRIPTION OF THE INVENTION

Figure 1:
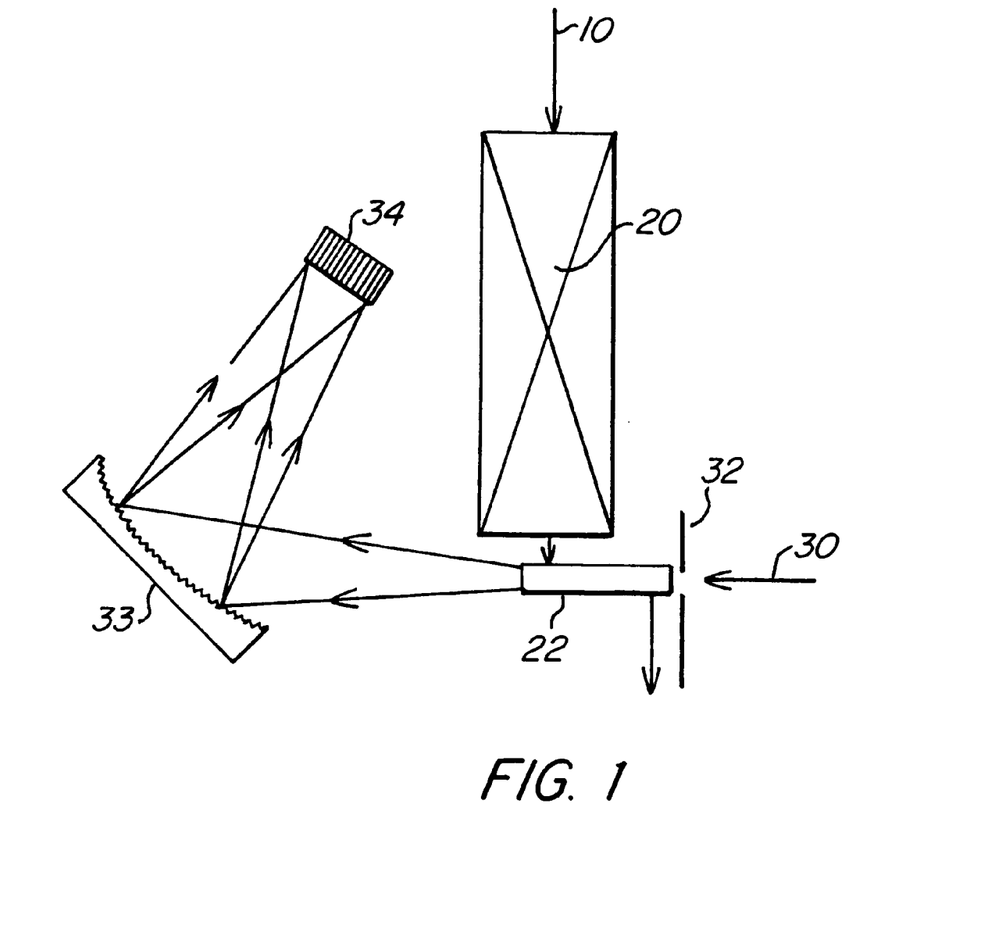
FIG. 1 is a simplified schematic representation of a sample eluted through a liquid chromatography (LC) column and analyzed by a spectrophotometer with a photodiode-array (PDA) detector.
Figure 2:
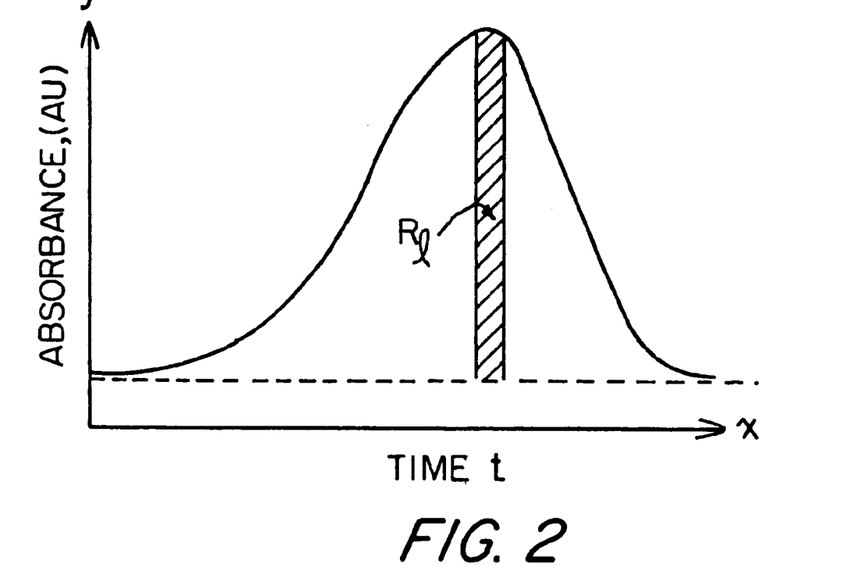
FIG. 2 represents a chromatogram of an analyte.

Detection of an impurity in an analyte using liquid chromatography (LC) in conjunction with a photodiode-array detector (PDA) involves analyzing the spectra and chromatographic profile of co-eluted compounds. FIG. 1 schematically shows a liquid chromatography (LC) column 20 with a flow-through cell 22 used with a UV-VIS spectrophotometer. The sample 10 is eluted or washed through the LC column 20 using a mobile phase of solvents. The particular chemical structure of any analyte in sample 10 when subjected to radiation 30 in the ultraviolet-visible (UV-VIS) range of 200–800 nm will have a characteristic spectral peak generated through an entrance slit 32 and grating 33 due to the sample's absorption of radiation when detected with a photodiode-array (PDA) detector 34. It is well known that a component's spectral absorbance is related to its concentration within the sample by Beer-Lambert's Law, represented as;

$$A = -\log_{10} I/Io = abc \quad (1)$$

wherein A is the component's absorbance, measured in absorbance units (AU);
I=intensity of the radiation emerging from the sample;
Io=intensity of the radiation without the sample;
a=molar absorption coefficient;
b=path length of the flow-through cell;
c=concentration of the analyte in the cell;

For a particular wavelength of light radiation emitted from the flow-through cell, an analyte contained in a sample will typically generate a characteristic measurement such as a chromatogram with a peak similar to that as shown in FIG. 2, where the y-axis dimension represents the absorbence of the component which correlates to its concentration, and the x-axis dimension represents elution retention time as the analyte is washed through the LC column. In addition, absorbance spectra for the analyte are generated as shown in FIG. 3, where the y-axis again represents the absorbance of the component, and x-axis represents a series of wavelengths attributable to the spectra generated. For the chromatogram, a baseline (represented as a dotted line in FIG. 2) is typically observed for any given component resulting from absorbance associated with the change in mobile phase and noise associated with the flow system or the PDA detector.

Figure 4:
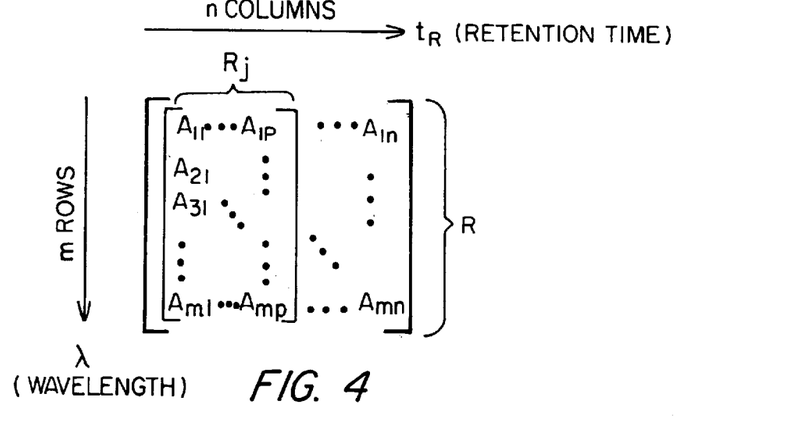
FIG. 4 illustrates the (m×n) matrix R which is a representation of the spectral space for the chromatogram spectra of the chromatographic peak.

The method of the present invention assumes that good linear additivity exists among a baseline, if any is present, major component(s), and any suspected impurity or impurities. In addition, the impurity to be detected must have a different spectral signature from any baseline and the major component(s) to be detected. The method of the present invention involves generating a (m×n) matrix R, shown in FIG. 4, which represents a spectral space generated by the chromatographic peak. The n columns of the R matrix represent the various retention times $t_R$ for a chromatographic peak, whereas the m rows of the matrix represent various detecting wavelengths on the PDA. Therefore, each point within the matrix represents a measured absorbance (AU) associated with a particular retention time for the LC elution and a spectral wavelength. A known start time ($t_0$) and end time ($t_1$) is selected to generate the matrix R, as well as a determination whether a baseline is present (in which case, $r_0$=1) or absent (in which case, $r_0$=0). In addition, a number for the major component(s), $r_1$, known or suspected to be in the analyte sample is selected. Typically, $r_1$=1, but the method of the present invention accounts for $r_1>1$. The expected total number of linearly independent components is given by:

$$r = r_0 + r_1 + 1 \geq r_{min} = 2 \quad (2)$$

Equation (2) represents the minimum number of spectra required on a chromatographic peak for impurity detection in the presence of only one major component without a baseline. Typically, a total of at least n>10 spectra are recorded between retention times $t_0$ and $t_1$. Once a value for $r_1$ is selected, and a peak impurity detection to be performed in a given spectral range is desired, at least m spectral points must be selected to generate the matrix R (dimensioned m×n) for each chromatographic peak identified, such that $m \geq r$, but more typically $m \geq 10r$.

Figure 5:
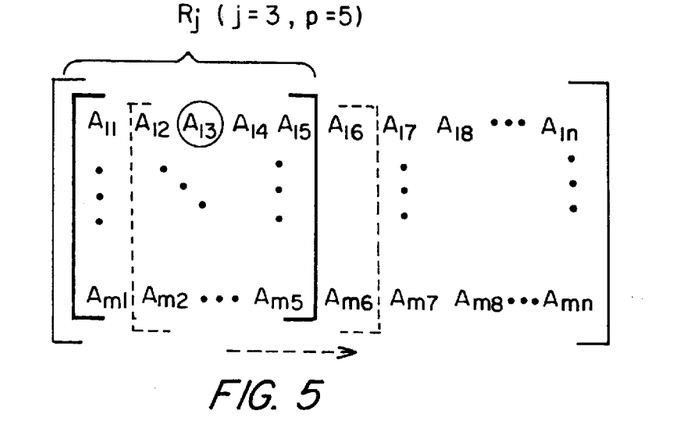
FIG. 5 illustrates the (m×p) sub-matrix $R_j$ which is applied as a sliding window giving rise to the spectral subspace represented by $R_j$.

Within the n columns of matrix R, a subset or small window, or sub-matrix $R_j$ containing an odd number of p columns representing consecutive time points of the elution chromatogram data within R, wherein $p \geq r$, can be repeatedly selected for analysis of the relation between the major component and the impurity such as to slide through the peak in search of the best sub-space for later spectral projection. What is meant herein by "best sub-space" is a set of vectors that best span the baseline (if any) and major components(s), i.e., the linear combination of these vectors can provide the closest approximation to all spectra in R in the absence of impurities. This search for a "spectral sub-space", or the generation of an $R_j$ matrix which changes its values as it moves consecutively from one set of p columns to another, is formed by taking the $[j-(p-1)/2]$ th to $[j+(p-1)/2]$ th column of the original matrix R, for each j where $(p-1)/2+1 \geq j \geq n-(p-1)/2$, which can then be decomposed via the technique of singular value decomposition (SVD) as known in matrix algebra, to:

$$R_j = U_j S_j V_j^T \quad (3)$$

Where $V_j$ is the right singular orthonormal matrix, dimensioned (p×q) containing sub-spaces in retention time where q=min(p,m) and superscript T represents the transpose of a matrix;

$S_j$ is a diagonal matrix, dimensioned (q×q) containing all positive singular values in descending order along its main diagonal and zeros elsewhere; and $U_j$ is the left singular orthonormal matrix, dimensioned (m×q) containing sub-spaces in wavelength.

The purity index or value $k_j$ is calculated by manipulating the matrix values of $S_j$ according to the equation;

$$k_j = \frac{\sum_{i=1}^{r_0+r_1} S_i}{S_r} \quad (4)$$

Where $r = r_0 + r_1 + 1$ and where $S_i$ is the i th element of the main diagonal of matrix $S_j$. $S_j$ can be represented as:

$$\begin{bmatrix} S_1 & 0 & \cdots & \cdots & 0 \\ 0 & S_2 & & & \vdots \\ \vdots & & \ddots & & \vdots \\ \vdots & & & \ddots & 0 \\ 0 & \cdots & \cdots & 0 & S_q \end{bmatrix} \quad (5)$$

An advantage to the matrix decomposition of $R_j$ into $S_j$ is that the overall baseline contribution to the total spectral response is allowed to change without affecting impurity detection provided that the spectral signatures of the baseline, i.e., the shape of its spectrum, remain the same throughout the peak.

The purity value $k_j$ will always be larger than 1.0000 and is calculated from equation (4) according to the number of expected component(s) in the peak, $r_1$, and whether a baseline exists, i.e., whether $r_0=0$ or $r_0=1$. A higher purity value $k_j$ corresponds to a purer segment of the chromatogram included in the sub-matrix $R_j$. However, a lower value for $k_j$ does not necessarily indicate an impurity due to the presence of noise in a baseline region which could cause a lower $k_j$ by division between comparably smaller singular values resulting from decomposition of a random matrix. Therefore, the $k_j$ value itself cannot serve as a peak impurity indicator, but can positively serve as a peak purity indicator to assess the purity of the peak where the maximum value, $k_l$, for $k_j$ can be selected as;

$$k_l = \max(k_j) \quad (6)$$

which corresponds to a sub-matrix $R_1$, as represented in FIG. 2, where $R_1$ contains the purest set of spectra across the whole peak.

Another aspect of the method of the present invention involves projecting every single full spectrum across the peak onto the spectral sub-space represented by $R_1$, corresponding to the purest set of spectra. It is from this projection that a residual spectrum can be calculated which reflects the amount of "spectral error", or departure from the spectra of the pure component(s) due to the presence of an impurity.

Figure 6:
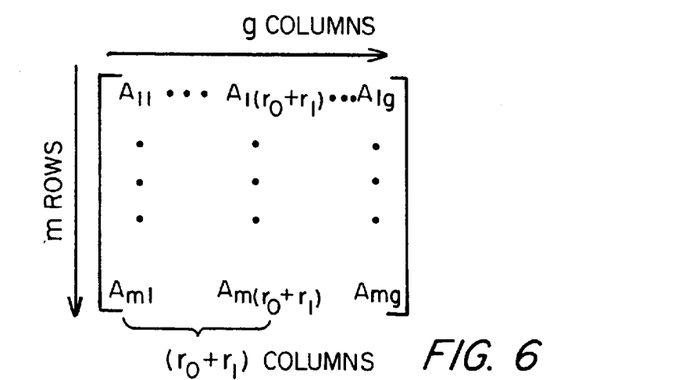
FIG. 6 illustrates the (m×(r0+$r_1$)) matrix U within the (m×q) matrix $U_j$.

An (m×m) projection matrix, $P_0$, is constructed by:

$$P_0 = UU^T \quad (7)$$

where U is dimensioned as $[m \times (r_0+r_1)]$ and formed by taking the first $(r_0+r_1)$ columns of the left singular matrix, $U_l$, (shown in FIG. 6), corresponding to the $R_1$ matrix representing spectral sub-space $R_1$, (shown in FIG. 2), wherein $U_l$ is determined and formed by selection of $R_1$ and a singular value decomposition on $R_1$ by the procedure outlined above.

Any spectrum r, represented as a (m×1) matrix that is made up of the same components, although perhaps in different portions, as those contained in the purer $R_1$ matrix, can be projected onto the spectral sub-space represented by the projection matrix, $P_0$, without being significantly changed where r is represented as;

$$r = P_0 r + e \quad (8)$$

and the residual e (m×1) should be at noise level. The equation can be rearranged into;

$$e = (I - P_0) r \quad (9)$$

$$P_1 = I - P_0 = I - UU^T \quad (10)$$

Letting,
e becomes;

$$e = P_1 r \quad (11)$$

where $P_1$ becomes a projection matrix that can be used to calculate the part of any spectrum r that is orthogonal to the sub-space $P_0$. Therefore this step derived from the manipulation of the spectral data actually gathered and represented in the matrices described above, allows for the check of any spectrum that may contain some unique spectral feature, such as whether that spectral feature is a result of an impurity. This unique part of the spectrum is the "net analyte signal" and is necessarily smaller than the pure spectral response for the suspected impure component because any part of the pure spectral response for the suspected impurity that is correlated with those already contained in the derived sub-space $P_0$ has been removed from the projection onto $P_1$ which is orthogonal to $P_0$. When there are no impurities with a unique spectral feature, the calculated residual e will be at the system noise level.

A root mean squared error can be calculated from this residual e to reflect an overall spectral error, calculated as;

$$E = \sqrt{\frac{e^T e}{n - r_0 - r_1}} \quad (12)$$

where E represents the peak impurity index (in absorbence units), caused by the presence of the suspected impurity.

This spectral error E can be readily calculated and used as a peak impurity indicator or index for each spectrum r contained within the spectral space represented by matrix R once the projection matrix $P_1$ has been constructed as outlined above. The most consuming part of the computation as applied to a computer with this method for detecting LC impurity is the calculation of the $k_j$ values associated with the sliding window across the whole peak. Should this pose a problem for a modern computer, which is unlikely, a singular value decomposition (SVD) updating algorithm could be applied as exactly one spectrum moves in and out in each successive movement of the window which frames the analysis for forming the sub-matrix $R_j$.

The above method of the present invention allows detection and interpretation of a peak impurity as applied to various scenarios. In the case of a pure peak without an impurity, where there is a single component, i.e., where $r_0=0$ and $r_1=1$, the $k_j$ value measures the signal to noise ratio, with the maximum $k_j$ occurring at the peak's maximum. In addition, each column or row in the projection matrix $P_0$ would be a scaled version of the same spectrum of the pure component. In the case of a mixture of components, where more than one component is to be detected, i.e., where $r_1>1$, a maximum $k_j$ value can be obtained at a retention time when the major component is still in abundance and the impurity is becoming negligible compared to the noise of the detection system.

Figure 3:
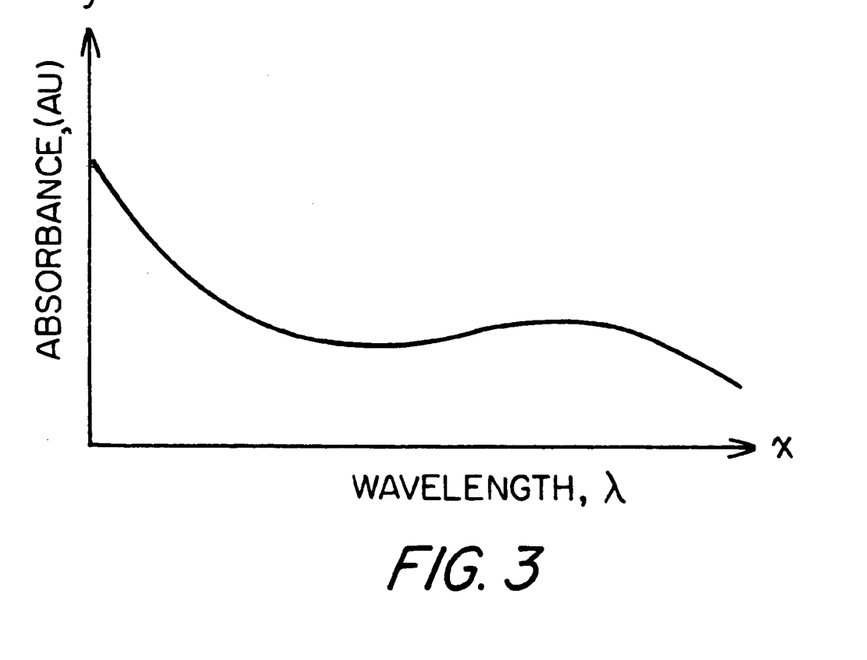
FIG. 3 represents a spectrum of an analyte at a given time, t.
Figure 7:
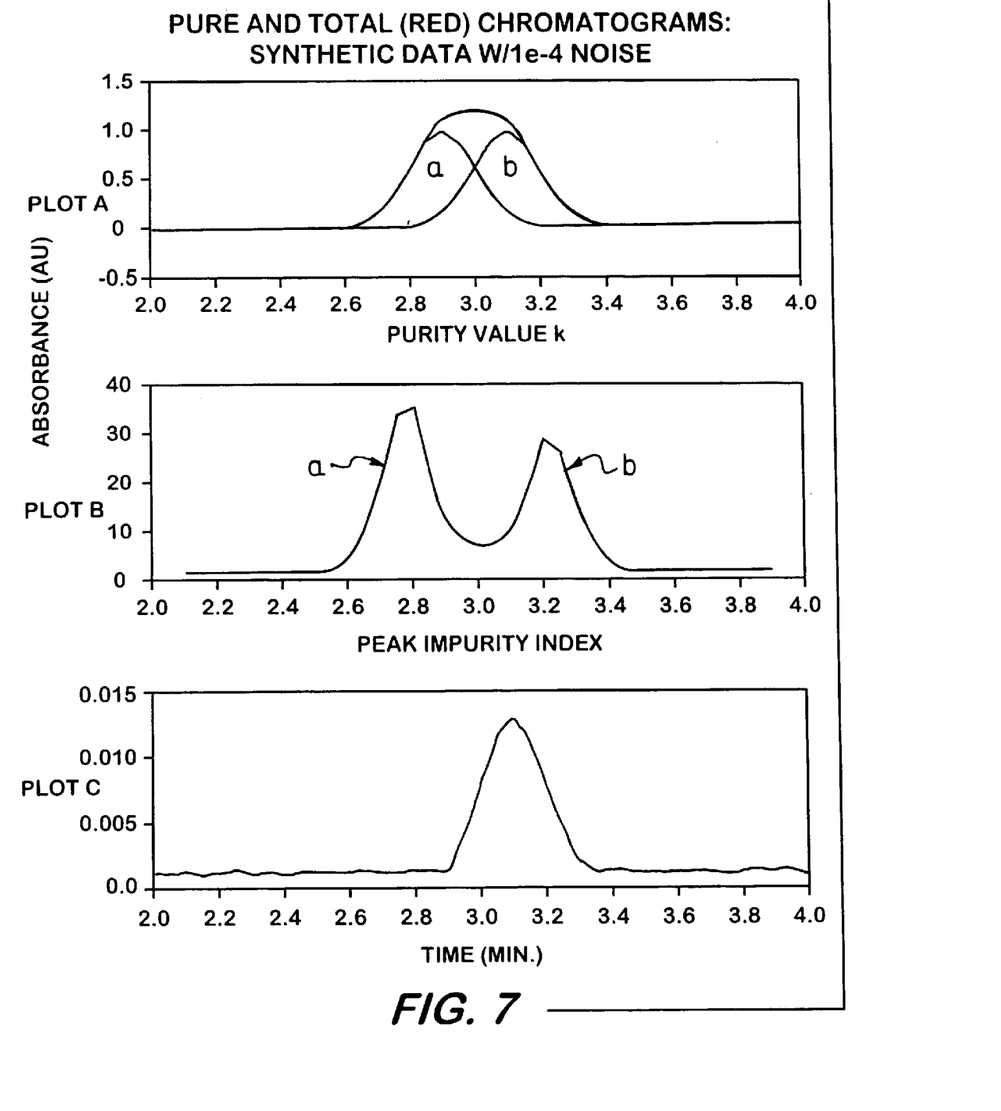
FIG. 7 in three panels is a series of plots A, B and C which respectively represent a chromatogram, a calculated purity value k, and an associated peak impurity index for a single component having an impurity.

FIG. 7, shows a plot of data synthesized according to the following matrix expression:

$$R = [S_1 S_2] \begin{bmatrix} C_1 \\ C_2 \end{bmatrix} + e$$

Where $S_1$ is dimensioned as a (m×1) matrix, and $S_2$ is dimensioned as a (m×1) matrix, and are pure spectra for component a and b (for example, as diagramed in FIG. 3).

$C_1$, dimensioned (1×n), and $C_2$, dimensioned (1×n), are the chromatograms of these two components modeled as Gaussians, and e, dimensioned (m×1) is the normally distributed noise term with mean of zero and standard deviation of $10^{-4}$ absorbance unit.

FIG. 7 shows plot A (the chromatogram of a pure component, a, with an impurity, b, underlying its total chromatogram with noise) with plot B (a plot of purity value k) and plot C (the peak impurity index, E,) for a sample. As seen in plot B, the peak purity value for component a is higher than for that of component b due to the fact that a has higher spectral sensitivity, i.e., greater absorbance for a given wavelength of radiation. Plot C shows that the peak impurity index will follow the general shape of an impurity's, b's, chromatographic profile as shown in plot A, but differs in that the rising part of the impurity index is reduced compared to its chromatogram when, such as in this example, part of the impurity's chromatogram overlaps with the first component's, a's, peak.

In the case of a mixture of components forming a peak composed of spectrally orthogonal components, e.g., no spectral overlap and no spectral contribution from the baseline, the peak impurity index can be exactly the same as the impurity chromatogram itself, the only difference being the scale between the two plots. In this special case, the peak impurity index as a unique spectral signature of an impurity is directly proportional to the concentration of the impurity. In such a situation, the values for $S_1$ and $S_2$ in the $S_j$ matrix will be nonzero and exactly proportional to the respective concentrations of components in the sample. In all other cases, as shown representatively in FIG. 7, the peak purity index provides a lower bound for the impurity's concentration in the sample.

Another advantage to the method of the present invention is that the baseline region associated with the chromatogram of the analyte sample will never be selected to span the sub-space $P_0$ due to the baseline's extremely low signal to noise ratio. Consequently, there is no requirement in the method to separately account for baseline contribution to detect an impurity, since the method of the present invention performs signal averaging or noise-filtering automatically by virtue of the algorithm as it is applied without causing numerical stability problems. What is meant herein by "numerical stability problems" is the numerical difficulty in dealing with mostly noise overwhelming a small signal.

The method of the present invention to detect an LC impurity is applied to two examples. In both examples, the spectral acquisition rate is about 2.2 spectra per second and the parameter p is set at 5 with $r_{min}=1$, i.e., one major component with no baseline. The experimental conditions used to generate the data contained in Examples 1 and 2, and as shown in FIGS. 7–10, are summarized in Table 1.

TABLE 1

| | Mobile Phase Composition | | |
|---|---|---|---|
| | MeOH | THF | Water |
| Example 1 | 50% | 14% | 36% |
| Example 2 | 75% | 0% | 25% |

The same sample is used in each example, and contains a mixture of benzene, touene, ethyl benzene, isopropyl benzene, tert butyl benzene, and anthracene.
Where MeOH=Methanol
THF=Tetrahydrofuran
A Perkin Elmer Series 200 diode array detector (DAD) is used for detection.

Figure 8:
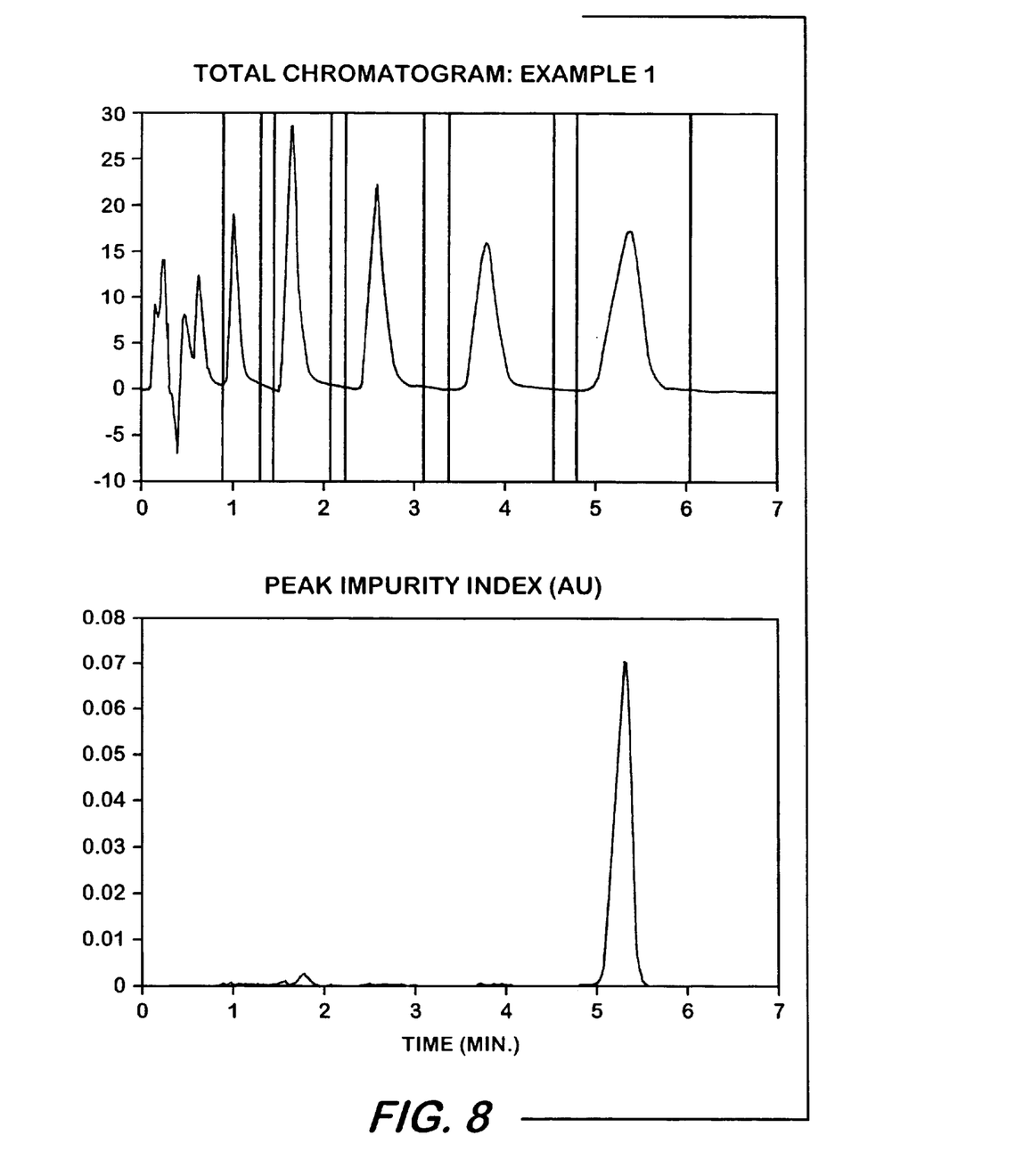
FIG. 8 in two panels is a multi-peak chromatogram and its associated peak impurity index plotted for a first example sample.

FIG. 8 shows the total chromatogram and peak impurity index E for Example 1. As shown in the total chromatogram of FIG. 8, five peaks (the start and end of each are marked with bolder vertical lines) are selected for peak impurity detection. There is an obvious impurity in the last peak, Peak No. 5, that gives out spectral error approaching 0.07 AU as shown in the peak impurity index plot of FIG. 8.

Figure 9:
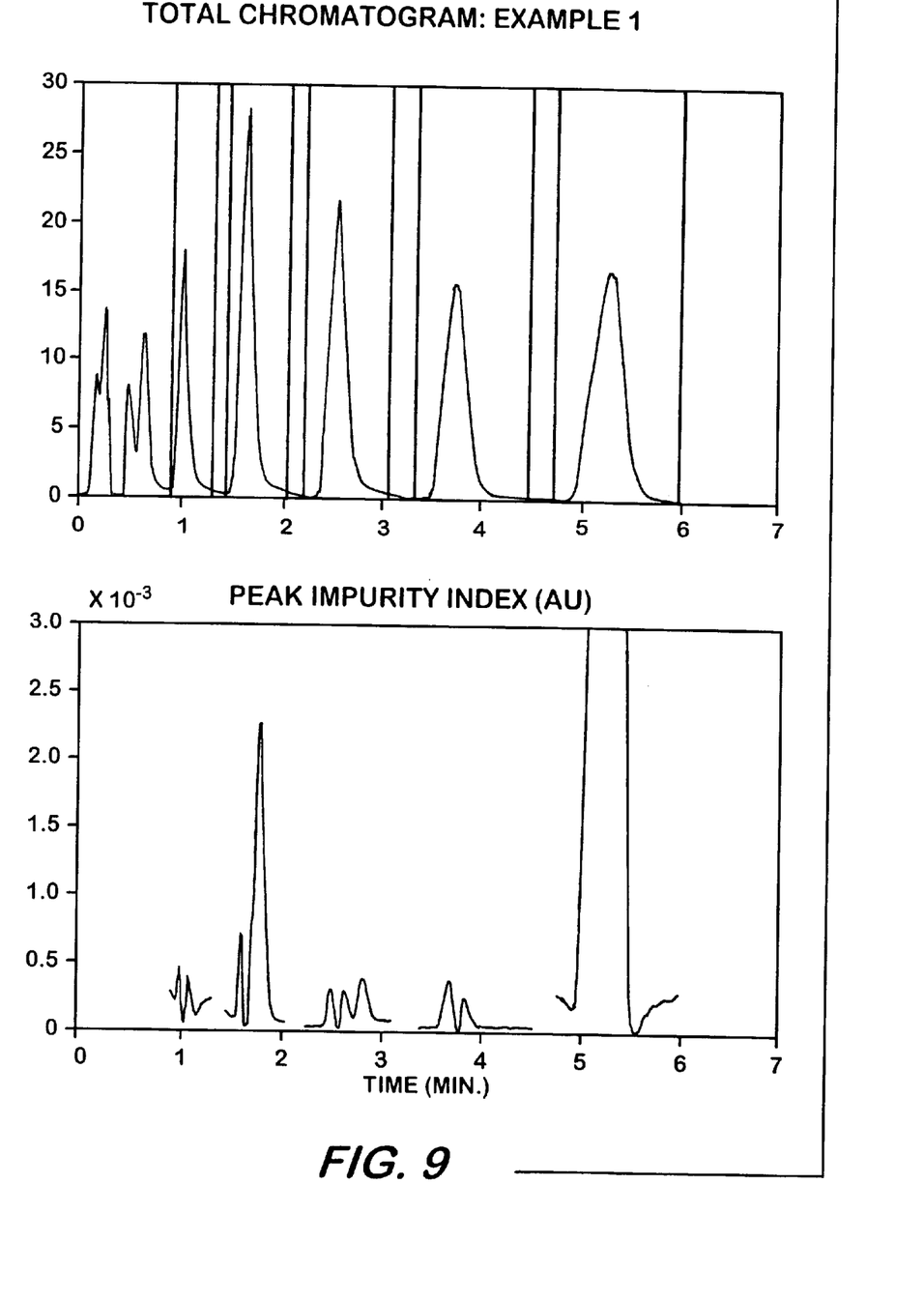
FIG. 9 in two panels is the chromatogram and peak impurity index of FIG. 8, wherein the peak impurity index is plotted against an expanded absorbance (AU) scale.

FIG. 9 shows the same chromatogram and peak impurity index E for Example 1 but at an expanded AU unit scale in order to better observe the shape of the much lower peak impurity indices E for Peaks Nos. 1–4. Peak No. 4 gives very small spectral error (less than 0.0005 AU) indicating a pure peak. The small second derivative structure of Peak No. 4 is however not random, and is perhaps related to minor artifacts due to the changes in component concentrations across a peak. Peak No. 1 has a similar spectral error that is of the same shape as Peak No. 4 and can be considered as a pure peak. Peak No. 2, on the other hand, has a large error above 0.002 AU, indicating presence of impurity. Peak No. 3 shows small spectral error and the presence of peak impurity can not be concluded.

Figure 10:
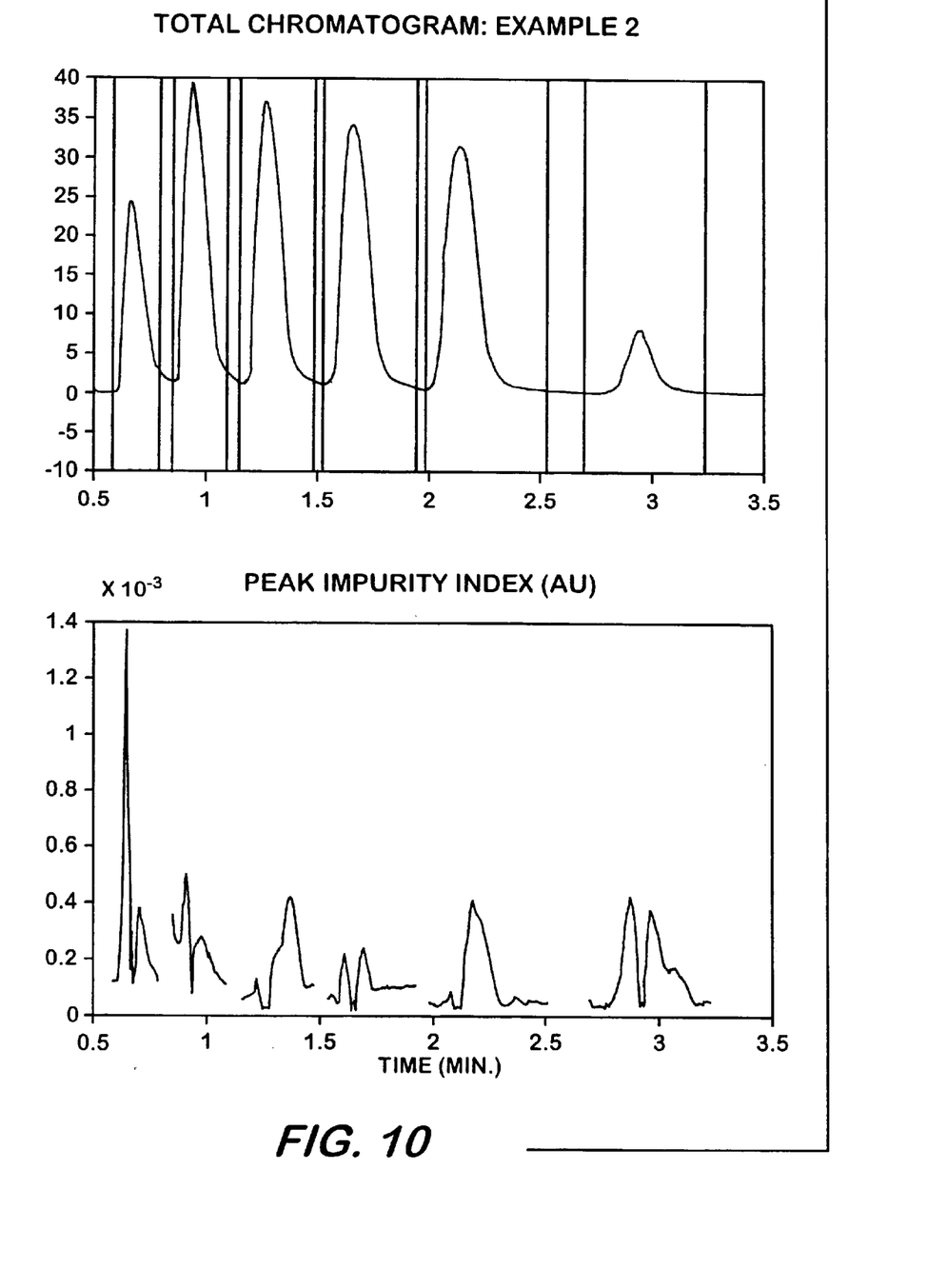
FIG. 10 in two panels is a multi-peak chromatogram and its associated peak impurity index plotted for a second example sample.

FIG. 10 shows the total chromatogram and peak impurity index E for Example 2. In Example 2, Peaks No. 2–6, bounded by the vertical lines, all have relatively small spectral errors and can therefore be considered as pure peaks. Peak No. 1 contains an obvious impurity, coming possibly from the tail end of the preceding peak.

It is understood that the method of the present invention is not specifically limited to detection of an impurity in an LC application but could be applied to any analytical method, which can detect a sample's components through multiple variable characteristic measurement. As an example and not as a limitation to the present invention, the method could be applied to 1) adsorption separation, 2) membrane separation, 3) affinity chromatography, 4) electrophoresis, 5) gas chromatography, and other separation techniques. Moreover, the method of the present invention is not specifically limited to application with a UV-VIS photodiode-array detector but could be applied to any analytical detection technique where a sample's components are determined by a characteristic measurement associated with at least two variables, as an example, and not as a limitation of the present invention, the method could be applied to FTIR spectroscopy, fluorescence, mass spectrometry, electrochemical detection, NMR, photoacoustic detection, circular dichroism, and other analytical techniques.

What is claimed is:

1. An apparatus for detecting an impurity in a sample having at least one component comprising:
    a device for obtaining characteristic measurements for the sample;
    a computer linked to said device;
    software executing on said computer for selecting a value representing an anticipated number of components in the sample;
    software executing on said computer for generating a matrix representing said characteristic measurements for the sample, said characteristic measurements having at least two variables in each dimension;
    software executing on said computer for repeatedly selecting a subset within said matrix for analysis of the relation between the component and impurity;
    software executing on said computer for constructing a projection matrix by projecting each of said characteristic measurements of said matrix onto said subset to calculate a residual error; and
    software executing on said computer for calculating an index from said subset to assess purity of the sample.

2. The apparatus of claim 1 wherein said characteristic measurement contains a baseline component.

3. The apparatus of claim 1 wherein said characteristic measurement does not contain a baseline component.

4. The apparatus of claim 1 wherein said characteristic measurements are spectra associated with a chromatographic peak.

5. The apparatus of claim 1 wherein said subset is represented by sub-matrix $R_j$ having values which can be decomposed into the expression:

$$R_j = U_j S_j V_j^T.$$

6. The apparatus of claim 4 wherein said matrix is dimensioned with data representing retention times for the chromatographic peak and wavelengths for the spectra.

7. The apparatus of claim 1 further comprising software executing on said computer for calculating a residual error e according to the equation:

$$e = (I - P_0)r.$$

8. The apparatus of claim 5 wherein said sub-matrix $R_j$ changes its said values as it moves consecutively from one set of p columns to another such that said sub-matrix $R_j$ is formed by taking the [j−(p−1)/2]th to [j+(p−1)/2]th column of said matrix represented by R, for each j where $(p-1)/2 + 1 \geq j \geq n - (p-1)/2$.

9. The apparatus of claim 1 wherein said index represents a purity index.

10. The apparatus of claim 1 wherein said index represents an impurity index.

11. The apparatus of claim 10, wherein said impurity index is represented by E according to the equation:

$$E = \sqrt{\frac{e^T e}{n - r_0 - r_1}}.$$

12. The apparatus of claim 9 wherein said purity index is represented by $k_j$ and is calculated from $S_j$ according to the equation:

$$k_j = \frac{\sum_{i=1}^{r_0 + r_1} S_i}{S_r}.$$

* * * * *